United States Patent [19]

Wilkinson et al.

[11] Patent Number: 5,198,011

[45] Date of Patent: Mar. 30, 1993

[54] METHODS FOR INHIBITING RUST INFECTIONS OF PLANTS

[75] Inventors: Robert E. Wilkinson; John J. Roberts, both of Griffin, Ga.

[73] Assignee: The United States of America as represented by the Secretary of Agriculture, Washington, D.C.

[21] Appl. No.: 226,608

[22] Filed: Aug. 1, 1988

[51] Int. Cl.$^5$ .................... A01N 55/06; A01N 41/04; A61K 31/305; C12N 9/99
[52] U.S. Cl. ........................................ 514/496; 514/1; 514/468; 514/762; 47/58; 435/184; 504/297; 504/357
[58] Field of Search ................... 71/65, 78, 79, 92, 80, 71/3; 435/184, 254, 911; 47/58; 514/564, 1, 496

[56] References Cited

U.S. PATENT DOCUMENTS 4,818,770  4/1989  Weinstein et al. .................. 514/564

OTHER PUBLICATIONS

Custom Applicator (May 1986) vol. 16(5): 40–42.
Fluka Chemika-Biochemika Catalog 16 (1988) item #25015 p. 344.
Gopal, et al. (1983) Indian Phytopathology 36: 732–734.
Pike (1981) Biochemical and Biophysical Research Communications 100: 1713–1719.
Eglinton et al., "Hydrocarbon Constituents of the Wax Coatings of Plant Leaves: A Taxonomic Survey," 1 Phytochem. 89–102 (1962).
Herbin & Robins, "Patterns of Variation and Development in Leaf Wax Alkanes," 8 Phytochem. 1985-98 (1969).
Von-Wettstein-Knowles, "Genetic Control of $\beta$-Diketone and Hydroxy-$\beta$-Diketone Synthesis in Epicuticular Waxes of Barley," 106 Planta (Berl.) 113-30 (1972).
Tulloch, "Composition of Leaf Surface Waxes of Triticum Species: Variation with Age and Tissue," 12 Phytochem. 2225-32 (1973).
Tulloch & Hoffman, "Leaf Wax of Triticum aestivum," 12 Phytochem. 2217-23 (1973).
Tulloch & Weenink, "Composition of the Leaf Wax of Little Club Wheat," 47 Can. J. Chem. 3119-26 (1969).
Netting and Von Wettstein-Knowles, "Biosynthesis of $\beta$-diketones of Barley Spike Epicuticular Wax," 174 Arch. Biochem. Biophys. 613-21 (1976).
Von Wettstein-Knowles, "Biosynthetic Relationships Between $\beta$-diketones and Esterified Alkan-2-ols Deduced from Epicuticular Wax of Barley Mutants," 144 Molec. gen. Genet. 43-48 (1976).
Mikkelsen, "Structure and Biosynthesis of $\beta$-Diketones in Barley Spike Epicuticular Wax," 44 Carlsberg Res. Commun. 133-47 (1979).
Von Wettstein-Knowles, "Genetics and Biosynthesis of Plant Epicuticular Waxes," Advances in the Biochemistry and Physiology of Plant Lipids, (Appleqvist & Liljenberg, eds. Elsevier, North Holland Biomedical Press, 1979).
Roberts et al. "Tolerance to Leaf Rust in Susceptible Wheat Cultivars," 74(3) Phytopathology 349-51 (1984).
Bianchi & Figini, "Epicuticular Waxes of Glaucous and Nonglaucous Durum Wheat Lines," 34 J. Agric. Food Chem. 429-33 (1986).
Long et al., "Virulence and Epidemiology of Puccinia recondita f.sp tritici in the United States in 1985," 70(12) Plant Disease 1107-10 (1986).
Roelfs et al., "The Rust of Wheat in the United States in 1987," Wheat Newsletter.
"Catching a Fungus in Action," Research Reporter 17.
Giaquinta, Plant Physiol. 57, 872-875 (1976).

Primary Examiner—Che S. Chereskin
Attorney, Agent, or Firm—Kilpatrick & Cody

[57] ABSTRACT

Methods are provided for inhibition of leaf rust infections of plants, especially wheat, using inhibitors which disrupt sulfhydryl bonds of the enzymes used by the leaf rust germ tube to ingest and metabolize components of epicuticular waxes.

5 Claims, 3 Drawing Sheets

METHODS FOR INHIBITING RUST INFECTIONS OF PLANTS

BACKGROUND OF THE INVENTION

This invention is generally in the field of methods for treatment of fungal infections in plants, especially rust infections of wheat.

Rusts are pathogenic parasitic fungi which infect wheat, barley, oats, beans, corn, sorghum, and other plants. Each rust is generally specific to its host and the location on the plant where infection occurs. Stem rust (*Puccinia graminis* f. sp. *tritici*) is a fungus which principally infects the leaf sheath of wheat plants. Leaf rust (*Puccinia recondita* f. sp. *tritici*) infects wheat plants through the stomates. Stripe rust (*Puccinia striiformis*) is similar to leaf rust but differs in that infections appear systemic due to colonization patterns on wheat leaves.

As shown in FIGS. 2 and 3, scanning electron photomicrographs courtesy University of Minnesota SEM lab, rust spores germinate on the waxy surface of the plant, forming germ tubes which migrate laterally across the surface to the stoma where an appressorium is formed. A structure known as an infection peg grows downward through the stoma from the appressoria following chromosomal and protein changes within the appressoria. The peg forms a substomatal vesicle from which infection hyphae ramify inside of the leaf. Continued internal development leads to formation of subcuticular uredia which produce reinfecting urediniospores which are wind-disseminated after uredia rupture the epidermis.

Rust is a good parasite in the sense that it does not kill its host, but reduces yield by stealing nutrients from its host. The plant can be simultaneously infected with other parasites including smuts and other fungi. Powdery mildew, (*Erysiphe graminis*, also germinates, forms a germ tube, and rapidly develops an appressorium from which the peg is capable of directly penetrating the cuticle of the leaf, in contrast to the rust fungi which must penetrate the leaf through the stoma. Powdery mildew possesses a cutinase enabling it to effect direct penetration.

In 1986 and 1987, approximately 126,000,000 bushels of wheat in the United States were lost to three rusts, stem rust, leaf rust, and stripe rust, an economic loss of greater than $378 million dollars. Each year, major losses occur in some of the nation's wheat-providing states.

Methods presently in use to combat rust infections include 1) use of rust resistant cultivars, 2) topical application of fungicides, and 3) cultural practices. Unfortunately, due to the relatively high rate of mutation of the rust organism, completely new cultivars of wheat are needed every seven years. Fungicides, while effective, are expensive and must be applied as a preventative, even if it is not certain that the plants will be infected. Many of the compounds previously in use have been withdrawn by the EPA. Compounds which are now utilized are more easily degraded and therefore less harmful to the environment but are more acutely toxic to humans. Thus, fungicide applications are even less desirable than before.

The disadvantages and lack of success of these methods are apparent when one considers the huge economic losses which occur each year.

It is therefore an object of the present invention to provide methods and compounds for inhibiting or preventing rust infections.

It is another object of the present invention to provide methods and compounds which are safe, effective, and relatively inexpensive to use.

It is a further object of the present invention to provide methods to reduce rust infection which can be used alone or in combination to increase effectiveness and decrease the probability of developing resistance to the compounds.

It is a still further object of the present invention to provide methods and compounds which can be used topically, after infection occurs, to lessen reinfection.

SUMMARY OF THE INVENTION

Methods are provided to decrease leaf rust infections of plants, especially wheat, using inhibitors of the enzymes used by the leaf rust germ tube to ingest and metabolize components of epicuticular waxes, using ethylene or ethylene-like plant hormones to induce random appressoria formation at locations other than at the stomate, thus deterring successful infection, using genetic procedures to alter epicuticular wax composition, and/or using natural plant-growth regulators, precursors, or modifiers to modify epicuticular wax components.

The major lipid classes present in the epicuticular waxes of wheat (*Triticum aestivum* L.) were separated and assayed for their utilization by wheat leaf rust (*Puccinia recondita* Rob. ex Desm.) spore germ tubes (WLRSGT) to produce $^{14}CO_2$. Alkanes and esters were poorly utilized (39 and 31%, or less, respectively). -Diketones ( ), free fatty alcohols (FFAlc), HO- -diketones (HO- ), and free fatty acids (FFAc) were utilized between 71 and 100%. Wheat leaf rust infectivity correlated with and HO-contents with possible modification by FFAlc and FFAc contents.

Inhibition can be achieved by alteration of the epicuticular wax composition to decrease the compounds utilized by the leaf rust germ tubes, especially the -diketones and HO- -diketones, using techniques such as selective breeding and genetic manipulation with screening for the production or non-production of particular compounds, as well as application of selected plant-growth regulators which modify epicuticular wax compounds.

It was determined that ethylene induced appressoria formation by wheat leaf rust spore germ tubes. Maximum appressoria formation (50%) was attained at 0.9 nmol/135 ml with decreased appressoria formation at ethylene concentration above and below this value. This method provides a further means to reduce successful infection.

BRIEF DESCRIPTION OF THE DRAWINGS

FIG. 1 is a cross-sectional view of the chamber for measuring utilization of wax components by leaf rust germ tubes.

FIG. 2 is a scanning electron photomicrograph (640x) of a leaf rust germ tube migrating laterally across the surface of a leaf.

FIG. 3 is a scanning electron photomicrograph (640x) of a leaf rust germ tube which shows the extremely close association between germ tube and epicuticular wax.

DETAILED DESCRIPTION OF THE INVENTION

Figure 1:
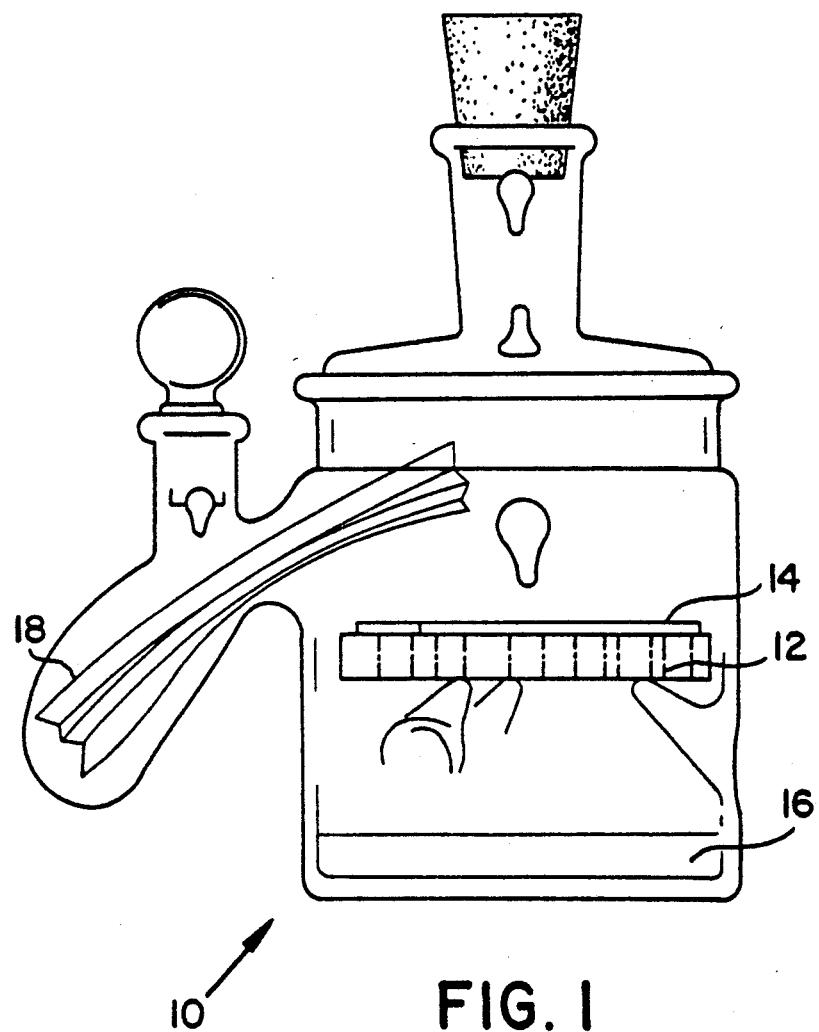

Rust infection of cereal plants, including wheat, barley, oats, a variety of beans, corn and sorghum, is a major problem for farmers, with only expensive, ephemeral and prospective means available for dealing with the problem. The present invention presents alternatives having a number of advantages over the available means: they can be used after infection occurs to prevent an epidemic, they are effective and relatively safe to the farmer, compound is not lost into the surrounding soil, plants can be treated by aerial spraying, and variations and combinations of the compounds can be utilized to decrease the chance of resistance rust strain developing.

One embodiment of the present invention uses enzyme inhibitors to decrease or block uptake of the epicuticular waxes by the migrating germ tube as it grows towards the stomate. The result is that fewer appressoria form and infection is therefore lessened. Compounds presently available are those which: 1) block the sulfhydryl groups on the germ tube enzyme(s), and 2) preferably do not penetrate the plant cell membranes. Compounds could also be developed using available technology to specifically inhibit the enzymes responsible for transporting and metabolizing the wax component, using the disclosed screening techniques.

These compounds could be applied to plants in fields using sprays formulated with any applicable carrier suited to the hydrophilic/lipophilic balance of the chemical. Sprays should be topical and designed to produce minimum coverage, penetration and maximum efficacy. The sulfhydryl inhibitor must not penetrate the membranes while the proposed plant growth regulator must penetrate into the cell. These two compounds could be incorporated into a single spray treatment. Commercial applications could be by aerial or ground systems.

Alternatively, plants can be selectively bred or genetically engineered to have an altered wax composition on the leaf surface. This must be contrasted with the methods now used to randomly generate and identify more resistant cultivars. Methodology and vectors are in use for inserting and modifying genes encoding the enzymes involved in wax synthesis. For example, Monsanto markets a vector for inserting genes into plants. The genetics and biosynthesis of plant epicuticular waxes are well characterized. See von Wettstein-Knowles, "Genetics and Biosynthesis of Plant Epicuticular Waxes", *Advances in the Biochemistry and Physiology of Plant Lipids*, Appelqvist and Lijenberg, ed. (Elsevier/North-Holland Biomedical Press 1979); von Wettstein-Knowles, *Molec.gen.Genet.* 144, 43–48 (1976); Mikkelsen, *Carlsberg Res.Commun.* 44, 133–147 (1979); Netting, et al., *Archives of Biochemistry and Biophysics* 174, 613–621 (1976); and von Wettstein-Knowles, *Planta (Berl.)* 106, 113–130 (1972).

As an alternative to genetic manipulation of epicuticular wax composition, selected gibberellic acid derivatives induce alteration in epicuticular wax composition by increasing or decreasing the quantity of individual wax component classes. Gibberellic acids (GA) are known to induce increased stem length. It is shown herein that GA also induces decreased total wax content (ng/plant) with an accompanying increase in -diketone concentration. A degradation product of GA$_3$ (GX) decreases -diketone content. Gibberic acid induces decreased -diketone content accompanied by an increase in total wax (ng/plant). The modification of leaf epicuticular wax composition by application of modified natural plant growth regulators (PGR) to attain a wax composition least favorable to the growth of the germ tube is demonstrated in the examples. These modified PGR do not have any other known influence on plant growth.

In another embodiment of the present invention, plants were exposed to ethylene or an ethylene-like compound to induce random appressoria formation at locations not over stomates. The compound can be applied in aerosol, gas or sprayed in solution. This technique can be combined with a compound which inhibits transport and/or utilization of epicuticular wax components to provide maximum inhibition of rust infection, or in combination with compounds which induce modification of wax composition. Since infection requires formation of appressoria over stomates, these combinations are effective by: 1) inhibiting the utilization of the wax components present, 2) inhibiting the synthesis of additional components (i.e., -diketones) that are highly utilized by rust germ tubes, and 3) inducing appressoria formation randomly but not necessarily over the stomates, thus reducing infection.

EXAMPLE I

Demonstration of Wheat Leaf Rust Spore Germ Tube Utilization of Epicuticular Wax Components as an Energy Source

*Puccinia recondita* Rob. ex Desm. urediniospores were sprayed onto wheat (*Triticum aestivum* L.) leaves and/or glass slides to which glycerol tri(1-$^{14}$C)palmitate or (1-$^{14}$C)linoleic acid had been previously applied and $^{14}CO_2$ was trapped. Germinating urediniospores and/or sporeling germ tubes were determined to utilize extracellular lipids as an energy source.

Wheat (*Triticum aestivum* L.) leaf rust (*Puccinia recondita* Rob. ex Desm.) urediniospores spores are very small and have limited food reserves having high energy content. Triacylgyceride content of stem rust (*P. graminis* f. sp. *tritici*) urediniospores declines during germination and germ tube development is dependent upon exogenous nutrients.

In the past, germination and sporeling development of wheat leaf rust spores have been presumed to be independent of leaf epicuticular wax contents. It has now been observed that several cultivars express patterns in which infection is greatest at the base of the flag leaf blade and least at the tip and that this pattern is directly correlated with epicuticular wax contents of grass leaves which grow from a basal meristem.

It was concluded from this observation, that some characteristic of wheat leaf epicuticular wax influenced spore germination and development. Since spores and sporelings utilize internal triglycerides as an energy source, it was decided to test whether they might also utilize portions of wheat leaf epicuticular waxes as an energy source.

Urediniospores.

Fresh wheat leaf rust urediniospores were supplied by the USDA-ARS National Cereal Rust Laboratory, St. Paul, Minn. Spores were suspended in deionized water to which two drops of the spreading agent, Triton X-100 were added. Germination counts were made on unstained material using the check slides.

Culture Chamber.

As depicted in FIG. 1, Warburg reaction chambers (135 ml) 10 were fitted with a perforated plexiglass support disk 12. Glass microscope slides 14 were cut to lay on top of the support disk 12. Wheat leaves were treated with $^{14}C$ containing lipid substrates and urediniospores were sprayed onto the leaves with an atomizer. The treated leaves were placed on the glass slides 14 which were positioned onto the support disk 12. 10 ml of water 16 was placed in the bottom of the flask 10. The reaction flask 10 was sealed and $^{14}CO_2$ was trapped in 10N KOH (3 ml 10N KOH on a piece of filter paper 18). After 24 hours at 28° C. (water bath), the filter paper +10N KOH was recovered and inserted into 18 ml scintiverse. $^{14}C$ was quantified by liquid scintillation spectroscopy (Beckman LS-100) for 50 minutes or 1% accuracy. Four replicates were utilized and data were statistically analyzed on a randomized block design.

Substrates.

$^{14}C$ was supplied as: a) glycerol tri(1-$^{14}C$)palmitate (60 mCi/m mol) (5 Ci/treatment), or b) [1-$^{14}C$]linoleic acid (56.7 m Ci/mg) (5 Ci/treatment). p-Chloromercuribenzenesulfonic acid (PCMBS) and dithiothreitol were applied at 1 and 10 mM concentrations, respectively.

Substrate Utilization.

Scanning electron photomicrographs of rust-inoculated wheat leaf surfaces showed what appeared to be germ tube tracks in the epicuticular wax, suggesting that germ tubes utilized epicuticular wax as a substrate. The presence of a living leaf is not necessary for urediniospore germination and germ tube development. However, the spores must contain a lipase to decompose the triglyceride so that fatty acids can be utilized as an energy source and some means of transferring the extracellular triglyceride and fatty acid into the germ tube must be present.

Germinating spore and germ tubes utilization of extracellular triglycerides and fatty acids as energy sources is shown in Table 1.

TABLE 1

Conversion of glycerol tri(1-$^{14}C$)palmitate and (1-$^{14}C$)linoleic acid to $^{14}CO_2$ by wheat leaf rust urediniospores on wheat leaves and glass slides

| | Glycerol-tri(1-$^{14}$)palmitate | (1-$^{14}C$) Linoleic acid | Spores | $^{14}CO_2$ Trapped (dpm) |
|---|---|---|---|---|
| Glass Slide | | | | |
| | − | − | − | 50 e[1] |
| | − | − | + | 175 d |
| | − | + | − | 432 c |
| | + | − | − | 540 c |
| | + | − | + | 13373 a |
| | − | + | + | 14649 a |
| Leaves | | | | |
| | − | − | − | 49 e |
| | − | − | + | 497 c |
| | − | − | − | 715 c |
| | + | − | − | 210 d |
| | + | − | + | 5135 b |
| | − | + | + | 7077 b |

[1]Values in a column followed by the same letter are not statistically different at the 5% level.

EXAMPLE II

Inhibition of Wheat Leaf Rust Spore Germ Tube Utilization of Epicuticular Wax Components as an Energy Source It is known that enzymes containing extracellular sulfhydryl groups are responsible for transferring apoplastic sucrose into phloem sieve tube elements. These extracellular sulfhydryl groups are oxidized by PCMBS, which is membrane impermeant. Dithiothreitol (DTT) (or dithioerythritol) prevents the activity of PCMBS on the extracellular sulfhydryl groups. These combinations were, therefore, evaluated for germ tube utilization of [1-$^{14}C$]linoleic acid as an energy source.

Impermeant PCMBS (1 mM) inhibited the conversion of [1-$^{14}C$]linoleic acid to $^{14}CO_2$ by 77% (Table 2). DTT induced a 9-10% increase in [1-$^{14}C$]linoleic acid conversion to $^{14}CO_2$. DTT reversed the inhibition by PCMBS so that spores treated with DTT PCMBS converted [1-$^{14}C$]linoleic acid into $^{14}CO_2$ at a rate equivalent to 83% of the conversion without either compound.

TABLE 2

Inhibition by p-chloromercuribenzenesulfonic acid (PCMBS) of wheat leaf rust spore conversion of (1-$^{14}C$) linoleic acid into $^{14}CO_2$ and the reversion of that inhibition by dithiothreitol (DTT)

| [1-$^{14}C$]Linoleic acid | PCMBS | DTT | $^{14}CO_2$ (dpm) |
|---|---|---|---|
| + | − | − | 18133 b[1] |
| + | + | − | 4126 d |
| + | − | + | 19857 a |
| + | + | + | 15076 c |
| − | + | − | 500 e |
| − | − | + | 475 e |
| − | − | − | 500 e |

[1]Values in a column followed by the same letter are not significantly different at the 5% level.

The conclusions drawn from these data are that the [1-$^{14}$-C]linoleic acid was transported into the germ tube by an enzyme containing extracellular sulfhydryl groups, PCMBS inhibited the activity of that enzyme, and DTT reversed the inhibition of PCMBS.

It is therefore possible to inhibit germ tube growth (and subsequent infection) by exposing the infected leaf to compounds which inhibit sulfhydryl groups, taking care to select those which are not also toxic to the plant and meet EPA requirements.

It should also be possible to inhibit germ tube growth by modifying the composition of the epicuticular wax of the host plant through: 1) PGR application, 2) genetic engineering, or 3) breeding with selection for altered epicuticular wax composition. von Wettstein-Knowles, p. 1-26 "Genetics and biosynthesis of plant epicuticular waxes", in L. Appleguist and C. Lilyenberg, editors, *Advances in the Biochemistry and Physiology of Plant Lipid*, (Elsevier/North Holland Biomedical Press, New York, N.Y. 1979). To facilitate this process, the composition and utilization of the epicuticular waxes by germ tubes were therefore determined.

EXAMPLE III

Utilization of Extracellular Lipids by Germinating *Puccinia recondita* Urediniospores $^{14}CO_2$ was utilized to label the epicuticular wax components of wheat (*Triticum aestivum* L., cvs. Coker 983, Florida 301, Red Bobs, and Hunter). The major lipid classes were separated and assayed for their utilization by wheat leaf rust (*Puccinia recondita* Rob. ex Desm.) spore germ tubes (WLRSGT) to produce $^{14}CO_2$. Alkanes and esters were poorly utilized (39 and 31%, or less, respectively). -Diketones ( ), free fatty alcohols (FFAlc), HO- -diketones (HO- ), and free fatty acids (FFAc) were utilized between 71 and 100%. Wheat leaf rust infectivity correlated with and HO- contents with possible modification by FFAlc and FFAc contents. -Diketone contents increased from the tip to the base of Coker 983 flag leaves. Esters were most concentrated at the tip and least concentrated at the mid- and base-sections.

Figure 3:
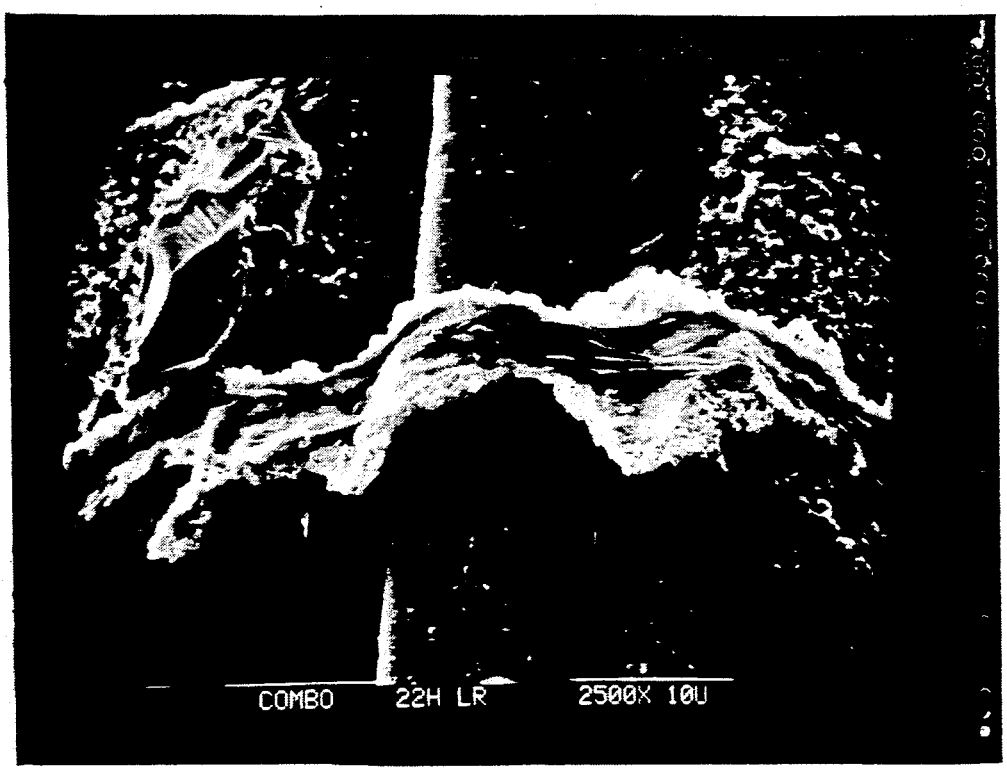
Figure 2:
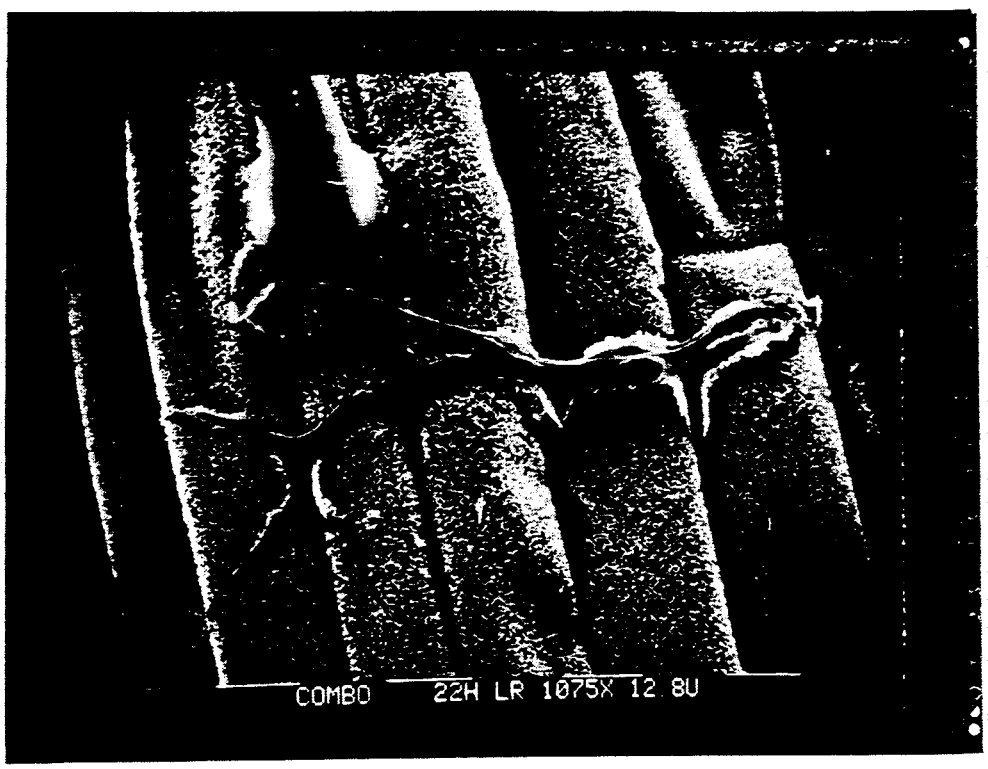

It was observed that wheat leaf rust spores infect the base of the flag leaf of some slow-rusting cultivars more heavily than the tip. This observation, in combination with the determination that wheat leaf rust spore germ tubes (WLRSGT) utilize epicuticular lipids as an energy source and that utilization is inhibited by p-chloromercuribenzenesulfonic acid (PCMBS) which is known to inhibit extramembrane enzymes containing sulfhydryl (SH) groups, and scanning electron photomicrographs providing evidence of intimate contact between germ tubes and epicuticular waxes (FIGS. 2 and 3) led to the hypothesis that germ tube growth was dependent on the availability of certain components of the epicuticular waxes.

Wheat and barley (*Hordeum vulgare* L.) epicuticular waxes are known to contain -diketones and HO- -diketones. These compounds are comparatively unique to cereals. Studies were therefore conducted to assess whether or not WLRSGT utilized other components of the leaf waxes, in addition to triglycerides and linoleic acid, as energy sources.

Methods and Materials:

Wax $^{14}C$ Content: Three wheat plants/pot (4 pots-/exposure) were grown in soil in the greenhouse to the boot stage (Feekes scale stage 10, that stage where the wheat spike or head is enclosed within the flag leaf sheath tube, just prior to the heading. cf. D. R. Tottman and R. J. Makepeace, "An Explanation of the Decimal Code for the Growth Stages of Cereals." *Am. Appl. Biol.* 93, 221-234 (1979)). The plants were placed in a 90 cm diameter clear polyethylene tube without being exposed to direct sunlight. The tube was sealed and 2 Ci $^{14}CO_2$ was released from $Na_2^{14}CO_3$ (10 mCi/mM) by concentrated HCl. After 18 h of exposure to $^{14}CO_2$, the plants were removed from the polyethylene tube and epicuticular waxes were recovered by chloroform extraction using the method of Martin, *J.Sci.Food Technol.* 11, 635-640 (1960). The solvent was evaporated to dryness and 10 ml $CHCl_3$ was utilized to liquify the residue. Lipid classes were separated by thin-layer chromatography according to the method of Tulloch and Hoffman, *Phytochem.* 10, 871-876 (1971) utilizing 0.25 mm silica gel g and chloroform:ethanol (99:1, v,v) as a developing solvent. The separated lipid classes were individually eluted into chloroform and concentrated with $N_2$. Four cultivars of wheat (Coker, 983, Florida 301, Red Bobs, and Hunter) were treated individually.

Lipid Substrate Utilization: As described previously with respect to FIG. 1, growth chambers were 135 ml Warburg flasks fitted with a perforated plexiglass disk. Ten ml water was added to the bottom of the flask and the side arm contained fluted (6 cm×4 cm) Whatman No. 1 filter paper +3 ml 10% KOH. Fifty 1 of a lipid were spread evenly over the surface of a glass slide (37.5 mm×25 mm) and the solvent was evaporated. Thirty mg urediniospores were mixed in 10 ml deionized water +2 drops Triton X-100 in an atomizer. After vigorous shaking, the spore suspension was evenly sprayed onto the glass slides which were then placed on the perforated plexiglass support. The chamber was sealed, placed in a 28° C. water bath, and the water bath was covered with black polyethylene. After an 18 h incubation, the filter paper was removed and inserted into a scintillation vial with 18 ml Scintiverse. $^{14}CO_2$ content was assayed by liquid scintillation spectrometry (Beckman LS-100) for 50 min or 1% accuracy after 24 h in the dark for fluorescence decay. Backgrounds were subtracted from the total DPM. Assays of each lipid class were conducted four times.

Coker 983 Wax Content: Coker 983 flag leaves, 19-20 cm long, were harvested from field-grown plants and weighed. Epicuticular waxes were extracted from three cm sections cut from the tip, middle, and base of the leaves in chloroform and the extract reduced to 10 ml. -Diketone content was quantitated by spectrophotometry (Beckman DB-GT) at 273 nm in quartz cuvettes with $E_{1\,cm}^{1\%}250$.

The lipid classes of the remainder were quantitatively separated by TLC, as described above. Internal standards (1 mg) (heptadecanoic acid, heptadecanol, or n-docosane) were added as required and fatty acid methyl esters or fatty alcohol formyl esters were prepared as described by Wilkinson and Mayeux in *Bot.-Gaz.* 148, 12-16 (1987). Esters were quantified by gas-liquid chromatography (Hewlett-Packard 5751A) using a dual FID detector and 0.32 cm diameter stainless steel columns 305 cm long filled with 5% OV-101 on 80/100 mesh Anakrom ABS. The column was programmed at 4° C./min with a 10 min upper limit hold. Detector and injector port temperatures were 380 and 370° C., respectively. Five replications were used throughout. Data were converted to g/g fresh weight.

Incorporation of $^{14}CO_2$ into epicuticular wax lipid classes (Table 3) shows alkane contents vary between cultivars (Coker 983 ¢ Florida 301 ¢ Red Bobs=-Hunter, 64.63, 41.31, 20.50, and 19.16 weight %, respectively). Ester $^{14}C$ content varied between 27.52 and 10.24%. -Diketone $^{14}C$ content was approximately inverse to the alkane contents (Coker 983 Florida 301=Red Bobs . Hunter; 5.33, 16.02, 15,82, 49.35 weight %, respectively). Various patterns were found for free fatty alcohols, HO- -diketones, and free fatty acids. The cultivars differed widely in their ability to incorporate $^{14}CO_2$ into epicuticular wax components (Total DPM/ml wax). The patterns shown in Table 3 are based on the assumption that the composition of the epicuticular wax follows the same pattern as the $^{14}CO_2$ application, at the time of $^{14}CO_2$ treatment.

TABLE 3

| | $^{14}C$ Content of Epicuticular Wax Lipid Classes | | | |
|---|---|---|---|---|
| Lipids | Coker 983 DPM (%) | Florida 301 DPM (%) | Red Bobs DPM (%) | Hunter DPM (%) |
| Alkanes | 6982 (64.63) | 3519 (41.31) | 470 (20.50) | 397 (19.16) |
| Esters | 2973 (27.52) | 872 (10.24) | 391 (16.62) | 366 (17.69) |
| -Diketones | 575 (5.33) | 1364 (16.02) | 362 (15.82) | 1022 (49.35) |
| Free Fatty Alcohols | 179 (1.66) | 1196 (14.04) | 778 (33.92) | 162 (7.82) |
| HO— -Diketones | 32 (0.30) | 502 (5.90) | 170 (7.44) | 81 (3.91) |
| Free Fatty Acids | 59 (0.55) | 1064 (12.49) | 130 (5.67) | 43 (2.08) |
| Total (DPM/ml) | 10800 | 8517 | 2292 | 2072 |

Lipid Substrate Utilization: WLRSGT utilized the $^{14}C$-lipid classes to produce $^{14}CO_2$ at different rates, as demonstrated in Table 4. Although, alkanes and esters were poorly utilized as energy sources to produce $^{14}CO_2$, the other four classes of lipid constituents in the epicuticular waxes were readily utilized to produce $^{14}CO_2$.

TABLE 4

Utilization of $^{14}$C-Lipid Classes Utilized to Produce $^{14}CO_2$ by Wheat Leaf Rust Spore Germ Tubes

| Lipids | Coker 983 | Florida 301 | Red Bobs | Hunter |
|---|---|---|---|---|
| | % $^{14}$C applied | | | |
| Alkanes | 38.9 | 1.0 | 0.3 | 23.8 |
| Esters | 30.8 | 4.5 | 6.0 | 13.6 |
| -Diketones | 70.8 | 62.8 | 21.8 | 72.0 |
| Free Fatty Alcohols | 98.0 | 99.0 | 99.0 | 99.0 |
| HO- -Diketones | 98.0 | 99.0 | 99.0 | 98.0 |
| Free Fatty Acids | 99.0 | 98.0 | 76.9 | 99.0 |

Comparison of wheat leaf rust infection with various combinations of -diketones, free fatty alcohols, HO- -diketones, and free fatty acids (Table 5) shows that combinations of these constituents, generally, correlate with infectivity. However, -diketone+HO- -diketone levels have a very close correlation with relative infection.

TABLE 5

Comparison of Wheat Leaf Rust Infectivity Between Wheat Cultivars and the $^{14}$C Contents of Selected Epicuticular Wax Components

| Cultivar % | Leaf Rust % | A | B | C | D |
|---|---|---|---|---|---|
| | | % $^{14}$C Content | | | |
| Florida 301 | 10 | 12.4 | 2.6 | 2.3 | 5.6 |
| Coker 983 | 40 | 7.8 | 2.5 | 2.1 | 10.2 |
| Hunter | 90 | 63.1 | 13.8 | 9.9 | 23.2 |
| Red Bobs | 100 | 62.9 | 46.7 | 42.7 | 53.2 |

A = -Diketones + Free Fatty Alcohols + HO- -Diketones + Free Fatty Acids
B = Free Fatty Alcohols + HO- -Diketones + Free Fatty Acids
C = Free Fatty Alcohols + Free Fatty Acids
D = -Diketones + HO- -Diketones Coker 983 Wax Content: Wheat leaf rust infection severity increases from the tip to the base of the flag leaf in some cultivars. The -diketones and HO- -diketones are intimately associated with infection efficiency and utilization of the wax as an energy source. Contents of these constituents would be expected to increase from the tip of the leaf toward the base, as shown in Table 6. Additionally, there are minor decreases in total alkane content from the tip to the base (Table 7), as compared to $^{14}CO_2$ incorporation into alkanes, shown in Table 3, and significant decreases in ester content from the tip to the base of the flag leaf (Table 7). -diketone content (in g/g FW) more than doubled form the tip to the base (Table 7).

TABLE 6

-Diketone Content of Coker 983 Flag Leaves

| leaf portion | -Diketones | HO- -Diketones |
|---|---|---|
| | g/g FW | |
| Tip | 1.4 c | 0.7 b |
| Mid | 3.1 b | 0.4 c |
| Base | 5.4 a | 1.0 a |

TABLE 7

Coker 983 Flag Leaf Epicuticular Wax Contents

| Lipids | Leaf Base | Mid-Leaf | Leaf Tip |
|---|---|---|---|
| | | wt. % | |
| Alkanes | 3.10 | 6.74 | 4.11 |
| Esters | 13.83 | 12.81 | 46.53 |
| -Diketones | 57.42 | 57.43 | 23.38 |
| Free Fatty Alcohols | 10.53 | 14.06 | 9.50 |
| HO- -Diketones | 10.99 | 7.93 | 11.00 |
| Free Fatty Acids | 4.13 | 1.03 | 5.58 |
| Total (g/g FW) | 9376.5 | 5349.4 | 6004.4 |

Wheat leaf rust urediniospores are very small with very limited internal food reserves usually in the form of triglycerides. Utilization of an external substrate source is beneficial to the organism during the infection process. Adaptation to utilization of the external food sources present on host species most conducive to growth and infection by the rust species provides it with a real selective advantage. -Diketones have been analyzed from several wheat cultivars and found to have a very limited range of constituents. Adaptation to these relatively unique energy sources would serve as a real and positive selection mechanism in the WLRSGT as it grows laterally across the wheat leaf until it finds a stoma where appressorium formation and penetration into the leaf occurs. Thus, under standard conditions, alterations in wax composition that are beneficial to WLRSGT would increase the range of the germ tube and, presumably, the relative chances of successful infection. Conversely, development of cultivars having fewer favorable wax components offers another means to reduce damage from rust infection. Such relatively complex changes in the nature of the leaf surface may pose a more difficult puzzle to the rust, making this a long-lasting form of partial resistance of potential value in supplementing other, more conventional forms.

EXAMPLE IV

Ethylene Induction of Appressoria Formation by Wheat Leaf Rust (*Puccinia recondita* Rob. ex Desm.) Spore Germ Tubes Wheat leaf rust urediniospores produce germ tubes which grow laterally across the wheat leaf surface. When the germ tube encounters a stomate, an appressorium is formed. Appressoria formation has been induced by acrolein, contact with stomate ridges, teflon, and an "effluvium" from stomates.

Ethylene is a gaseous plant growth regulator produced by plants, which induces a variety of responses including cessation of horizontal growth. Plant responses to ethylene depend highly upon concentration, tissue, and species. Ethylene was evaluated to determine the influence of ethylene on leaf rust spore germ tube elongation and appressoria formation.

Methods and Materials.

Culture: Using a 135 ml Warburg flask fitted with a perforated polystyrene disk+10 ml deionized water (as described before with reference to FIG. 1), wheat leaf rust uredispores (10 ml water+2 drops Triton X-100) were sprayed onto glass microscope slides (37×25 mm) coated with petrolatum. The slides were prepared by heating on a slide warmer (65° C.) for 24 hours to produce an even petrolatum covering without ridges. The slides were placed into the chambers. The chambers were maintained at 28° C. in a water bath and darkened with a 5 mil black polyethylene cover.

After an 18 h germination, ethylene was inserted into the chambers, the chambers were resealed and covered, and development was continued for 7 hours. Fifty mg urediniospores per 10 ml water were used in studies 1 and 2, and 100 mg urediniospores/10 ml water were used in study 3. Each test was conducted in quadruplicate.

Urediniospore Counting: Slides were dipped for 8 seconds in acid fuchsin to stain germinated structures. Counts were made at 430x of germ tubes and germ tubes with appressoria. Only those which could be linked to a spore were included.

Study 1: Ethylene was inserted after 4 hr growth at concentrations 100 nmol/135 ml. All spore germ tube growth ceased under these conditions, although untreated germ tubes grew normally with 5% appressoria formation. The conclusion was therefore that these ethylene concentrations were too high and initial spore tube growth was insufficient.

Studies 2 and 3: Urediniospore germ tube appressoria formation was induced 50% by 0.9 nmol/135 ml ethylene. Increasing or decreasing the concentrations of ethylene significantly decreased the percentage of germtubes that developed appressoria.

Stem rust produced appressoria at about 25% at the same ethylene concentration.

EXAMPLE V

Control of Wheat Leaf Epicuticular Wax Composition by Gibberellic Acid ($GA_3$) and its Degradation Products Wheat leaf rust urediniospores produce germ tubes which ingest epicuticular wax lipids as an energy source. Within the total waxes, two major biosynthetic schemes are know. One produces alkanes, esters, free fatty alcohols and free fatty acids, while the other produces the -diketone series of compounds. Gibberellic acid ($GA_3$) is known to induce the synthesis of glyoxysomes at specific plant growth stages which utilize the fatty acid base lipids to produce Ac-CoA.

Exogenous application of $GA_3$, a natural PGR, was therefore tested for alteration of the epicuticular wax composition of wheat leaves.

Methods and Materials:

Twenty-five wheat (cv Stacy) seeds were planted in sand in 10×10×10 cm pots and the initial watering was with 100 ml Hoagland and Aron complete mineral nutrient solution. After 10 days, the plants were sprayed with $GA_3$-methyl ester (0, 0.1, 1.2, 5, or 100M) in water (40 gpa) containing 3 ml Chem-nut oil per 250 ml water. Waxes were extracted in $CHCl_3$ and evaporated to dryness. The total wax (mg) was determined by weight and the -diketone content was determined spectrophotometrically.

In succeeding studies, gibberic acid (G) or a water soluble $GA_3$ degradation product (GX) was substituted for $GA_3$.

$GA_3$-Methyl Ester: $GA_3$-Methyl Ester induced a decreases in total wax (mg/plant) concentration without influencing -diketone concentration, as shown in Table 8.

TABLE 8

Influence of $GA_3$ on growth and epicuticular wax quantity and composition of wheat (*Triticum aestivum* L. cv Stacy).

| | | $GA_3$-Methyl Ester (M) | | | | |
|---|---|---|---|---|---|---|
| | Days | 0 | 0.1 | 1.2 | 5.0 | 100 |
| (Height) | 0 | 29.6 | | | | |
| | 0+2 | 27.0 | | | | |
| | 3 | 28.8a[1] | 29.8a | 29.8a | 28.8a | 28.6a |
| | 7 | 31.0c | 32.0c | 36.0b | 37.0b | 39.0a |
| Fresh Weight (mg/plant) | 0 | 227 | | | | |
| | 0+ | 209 | | | | |
| | 3 | 260c | 271b | 291a | 268c | 262c |
| | 7 | 312d | 325c | 329b | 357a | 319cd |
| Total Wax (mg/plant) | 0 | 8b | | | | |
| | 0+ | 8b | | | | |
| | 3 | 11a | 7b | 12a | 4ed | 2e |
| | 7 | 6bc | 5c | 4cd | 7b | 5c |
| -diketone (%) | 0 | 11.3d | | | | |
| | 0+ | 10.1de | | | | |
| | 3 | 9.4e | 15.7c | 11.0d | 19.4a | 17.5b |
| | 7 | 19.8a | 20.6e | 22.9a | 19.5a | 21.4a |
| Total Wax- -Diketones | 3 | 9 | 7 | 10 | 5 | 0 |
| | 7 | 4 | 4 | 3 | 5 | 2 |

[1]Values on a line followed by the same letter are not significantly different at the 5% level.
[2]Plants which received the water-Chemnut oil spray without $GA_3$.
Each value is the average of five replicates.

Gibberic acid (G) induced an increased total wax minus -diketones concentration but not an accompanying increase in -diketone concentration. As a result, the % -diketone content was drastically decreased, as demonstrated in Table 9.

TABLE 9

Influence of gibberic acid-methyl ester on the epicuticular wax composition of wheat (*Triticum aestivum* L. cv Stacy) leaves seven days after application.

| | Gibberic Acid-Methyl Ester (M) | | | | |
|---|---|---|---|---|---|
| Constituent | 0 | 0.1 | 1.2 | 5.0 | 100 |
| Total Wax- -Diketones (Δ g/plant) | 13d[1] | 249c | 362b | 307bc | 581a |
| -Diketones (%) | 25a | 17b | 16b | 11c | 9c |

[1]Values in a line followed by the same letter are not significantly different at the 5% level.
Each value is the average of five replications.

Neither G nor GB influenced plant elongation or increase in fresh weight. Induction of the synthesis of isocitric-lyase, a critical enzyme in glyozysomes involved with the -oxidation of fatty acids, by $GA_3$ is shown in Table 10.

TABLE 10

Influence of gibberellic acid ($GA_3$) on the isocitric lyase content of wheat (*Triticum aestivum* L. cv Stacy) leaks at 3- and 7-days after $GA_3$ application.

| Isocitric Lyase | | $GA_3$-Methyl Ester (M) | | | | |
|---|---|---|---|---|---|---|
| | Days | 0 | 0.1 | 1.2 | 5.0 | 100 |
| nmol product min mg-protein | 3 | 23.4a[1] | 18.8a | 22.6a | 23.7a | 21.4a |
| | 7 | 7.5c | 17.1a | 15.5a | 15.5b | 15.7b 10.7c |
| nmol product min g Fresh Weight | 3 | 1.0a | 1.3a | 1.3a | 1.3a | 1.1a |
| | 7 | 2.6c | 3.8b | 3.7b | 3.7b | 4.3a |

[1]Values in a line followed by the same letter are not significantly different at the 5% level.
Each value is the average of five replications with triplicate assays per relication.

TABLE 11

Influence of a $GA_3$ degradation product on the growth and epicuticular wax quantity and composition is seedling wheat (*Triticum aestivum* L. cv Stacy) grown in nutrient solution

| | | GX ( M) | | | |
|---|---|---|---|---|---|
| | Days | 0 | 1 | 10 | 100 |
| Height | 0 | 26.0 | | | |
| (cm) | 3 | 27.6a[1] | 27.0a | 28.2a | 28.2a |
| | 7 | 34.4a | 32.2a | 33.0a | 33.0a |
| Fresh | 0 | 211 | | | |
| Weight | 3 | 297a | 287a | 309a | 282a |
| (mg/plant) | 7 | 484a | 428b | 420b | 432b |
| Total wax | 0 | 469 | | | |
| (mg/plant) | 3 | 495a | 301b | 191c | 223c |
| | 7 | 484a | 428b | 420b | 432b |
| -Diketone | 0 | 6 | | | |
| (mg/plant) | 3 | 54a | 15b | 6b | 6b |
| | 7 | 57a | 12b | 9b | 7b |
| -Diketone | 3 | 100a | 19.2b | 0.2e | −0.6e |
| (%) | 7 | 100a | 17.4b | 8.8e | 5.0d |

This study demonstrates the alteration of the composition of epicuticular waxes by the topical application of natural plant-growth regulators or their precursors or degradation products. With the latter two compounds, no other response by plants is known.

Modifications and variations of the present invention, methods and compounds to inhibit leaf rust infections, will be obvious to those skilled in the art from the foregoing detailed description of the invention. Such modifications and variations are intended to come within the scope of the appended claims.

We claim:

1. A composition for inhibiting rust infection of plants comprising non-membrane penetrating compounds which disrupt extracellular sulfhydryl bonds in leaf rust proteins involved in utilization and transport of epicuticular wax components by leaf rust germ tubes.

2. The composition of claim 1 wherein the compound is in a carrier for application as an aerosol or spray.

3. A method for inhibiting rust infection of plants comprising providing a non-membrane penetrating compound which disrupts extracellular sulfhydryl bonds in leaf rust proteins involved in utilization and transport of epicuticular wax components by leaf rust germ tubes.

4. The method of claim 3 further comprising applying the compound to the plants to be treated for inhibition of rust infection.

5. The method of claim 3 further comprising preparing a solution of the compound.

* * * * *